United States Patent [19]
Boyd

[11] Patent Number: 5,795,150
[45] Date of Patent: Aug. 18, 1998

[54] INTRAORAL SEMI-CUSTOM DISCLUDER DEVICE AND METHOD

[76] Inventor: James P. Boyd, 800 W. Long Lake, No. 135, Bloomfield Hills, Mich. 48302

[21] Appl. No.: 805,887

[22] Filed: Mar. 3, 1997

[51] Int. Cl.$^6$ ..................................... A61C 3/00
[52] U.S. Cl. ..................... 433/6; 433/215; 128/861
[58] Field of Search ................. 433/215, 6; 128/848, 128/857, 861, 862, 859

[56] References Cited

U.S. PATENT DOCUMENTS

| | | | |
|---|---|---|---|
| 2,694,397 | 11/1954 | Herms | 128/861 |
| 4,773,853 | 9/1988 | Kussick | 433/6 |
| 5,067,896 | 11/1991 | Korn | 433/6 |
| 5,092,346 | 3/1992 | Hays et al. | 128/848 |
| 5,277,203 | 1/1994 | Hays | 128/861 |
| 5,624,257 | 4/1997 | Farrell | 433/6 |

*Primary Examiner*—Nicholas D. Lucchesi
*Attorney, Agent, or Firm*—John R Duncan; Frank D. Gilliam

[57] ABSTRACT

An intraoral semi-custom device for the prevention of chronic tension and common migraine headaches and temporomandibular disorders that are caused by chronic clenching of the posterior mandibular and maxillary teeth by the temporalis muscle. The device includes a trough, curved to correspond to the curvature of the maxillary incisors, from which distally extends a dome shape. The trough and dome are formed from a reshapable synthetic resin sheet material. The trough is retained by a cured in place acrylic resin, which is placed into the trough by a dentist and then placed over the maxillary incisors by the dentist. The cured, now substantially rigid, acrylic fits tightly and retains the device around the wearer's upper incisors. Once in place in the wearer's mouth, the dome will come into contact with one or two lower incisor teeth prior to the posterior teeth coming into contact. This renders the temporalis muscles ineffective, preventing high pressure clenching of the posterior teeth, thus preventing tension headache, common migraine, and temporomandibular disorders. While the device may be worn most of the time, including during sleep, it is not attached permanently and is always removed while eating, thus preventing supraeruption of the posterior teeth.

8 Claims, 1 Drawing Sheet

INTRAORAL SEMI-CUSTOM DISCLUDER DEVICE AND METHOD

BACKGROUND OF THE INVENTION

This invention relates in general to the prevention of tension and common migraine headaches and temporomandibular syndrome and, more specifically, to an intraoral, semi-custom device for preventing those conditions.

Many people suffer from recurring tension, or muscle contraction, headaches ranging from mild to severe. The severity of the headache often mimics the severity of classic migraine and can be diagnosed as "common migraine".

Tension is a muscular property. Muscles tense, or contract to do work. When a muscle contracts statically and continually, it will become painful. The intensity or degree of contraction and longevity of contraction will dictate the degree of discomfort.

The majority of the muscles that cover the human head (i.e., skull) are responsible for facial expression (raising eyebrows, etc.). These muscles are not strong enough to elicit the type of discomfort associated with headaches. There is an extremely powerful muscle, however, located on the side of the skull, extending from just behind the eye to just behind the ear. This muscle, the temporalis muscle, has one function, to close (or "elevate") the lower jaw. When isometrically contracted, the temporalis muscle can exert a tremendous amount of static force. This isometric contraction can only occur when the posterior mandibular and maxillary teeth or dentures are in contact with each other.

The common tension headache in the temporal region is caused by moderate to severe inappropriate contraction of the temporalis muscles. Under usual and normal circumstances, the upper and lower teeth should rarely, if ever, come in pressure contact other than during normal chewing. The inappropriate muscular activity that clenches the upper and lower jaws together along with their associated dentition is called myofascial dysfunction.

Clenching is a motionless act; therefore, it is practically impossible to notice another person clenching. Additionally, clenching is most commonly done while the person is concentrating on another topic, or while dreaming, so that it is very difficult to have a self awareness of clenching.

As the muscular contraction condition of clenching continues, the muscles become fatigued and susceptible to spasm and cramping. The pain from spasming temporalis fibers is quite severe and is usually diagnosed as common migraine. This type of migraine initiates as a severe headache that may last for two to three days. The muscle contraction headache patient, when seen by a physician, is usually treated with muscle relaxants and analgesics and may be referred to a physical therapist to treat the fatigues muscles. However, this treats the symptoms but does not address the cause.

These patients, when seen by a dentist, are commonly diagnosed as having temporomandibular disorder. These patients are typically treated with an intraoral "jaw-positioning" appliance. Typical of these are the orthotics or splints described by Norton in U.S. Pat. No. 4,671,766 and Sullivan in U.S. Pat. No. 4,519,386. The appliance, or splint, covers either the upper or lower posterior teeth. Unfortunately, the upper and lower jaws are approximated by way of the splint, thus allowing the clenching to persist, and in many cases, intensify.

Applicant's prior patent (Boyd, U.S. Pat. No. 5,085,584) describes a device that is effective in preventing clenching. Unfortunately for the sufferer, the device is complex and must be custom fabricated for each individual patient by a dentist, usually at a prohibitive cost (several hundred dollars) to the majority of sufferers. An improved discluding device, as described in Boyd U.S. Pat. No. 5,513,656, simplified the discluder and was capable of being fitted by the user. While less expensive to make and fit, problems remained in excessive flexibility and movement in use. The flexibility has been found to encourage undesired temporal muscle activity. In addition, the flexible silicone material had a tendency to absorb moisture and encourage fungal growth with extended use. With long-term use, the silicone rein sometimes would peal off of the trough.

Thus, there is continuing need for simplifying and improving means and methods for the prevention of clenching and the resultant headaches, which inhibits temporal muscle activity, which will perform well for extended periods without requiring repair and continuing to resist growth of fungi.

SUMMARY OF THE INVENTION

The above-noted problems, and others, are overcome in accordance with this invention by a small intraoral, semi-custom device that inhibits inappropriate isometric contraction of the temporalis muscles and is more effective and long lived. The device includes a prefabricated trough, curved to correspond to the general curvature of the four anterior maxillary incisors. The trough is retained on the teeth by the placement of a substantially rigid acrylic resin within the trough which when placed over the teeth forms a sealing gasket, which then retains the trough on the teeth. Extending distally from the trough is a small dome shape that extends such that as the jaws come together, the lower (mandibular) anterior incisal teeth edges come into contact with the dome prior to the upper and lower posterior teeth coming into contact. This maintains the separation, or disclusion, of the posterior teeth and prevents clenching. The dome can be modified by the wearer so that disclusion is maintained in all mandibular excursive movements.

The device must be removed by the wearer when eating. The device can be installed at all other times, in particular, during stressful occasions and when sleeping.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
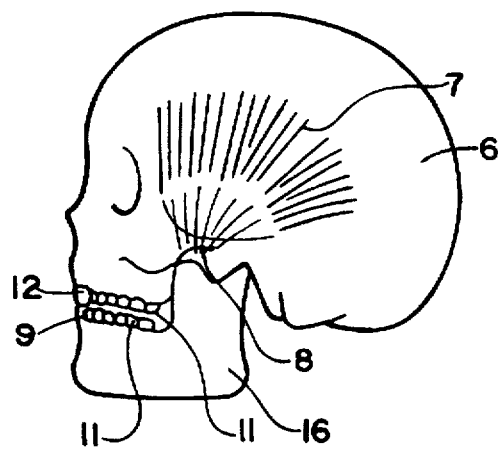
FIG. 1 is a schematic side view elevation of the human skull with the semi-custom discluder device of this invention in use.

Referring now to FIG. 1, there is seen a schematic representation of a human skull 6. The temporalis muscle 7 extends from the skull to its attachment 8 on the mandible (jaw) 16, with contraction of the muscle 7 causing the jaw 16 to close. When the semi-custom discluder 12 of this invention (as detailed in FIGS. 2–4) is in place along the anterior maxillary teeth 10 in FIG. 1 and FIG. 5, only the anterior portion and perhaps the dome 13 is seen. As is apparent, the lower anterior teeth 9 contact the dome 13, preventing posterior teeth 11 from coming into contact.

Figure 2:
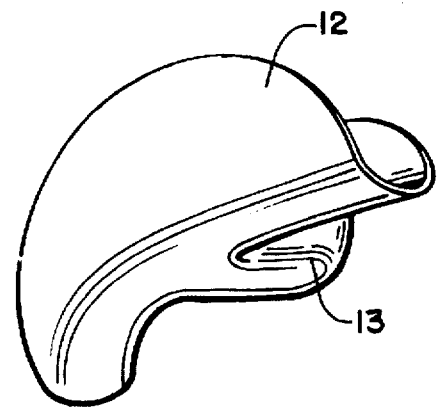
FIG. 2 is a perspective view of the semi-custom discluder device seen from the left-front-interior.
Figure 3:
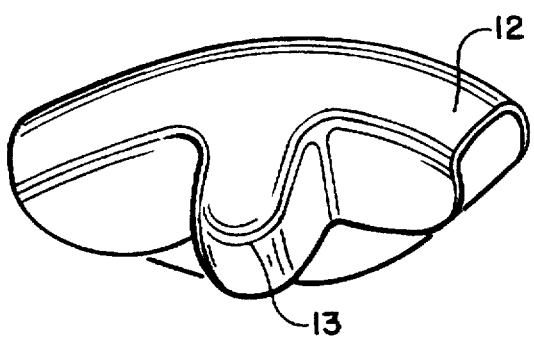
FIG. 3 is a perspective view of the semi-custom discluder device seen from the inferior-posterior.
Figure 4:
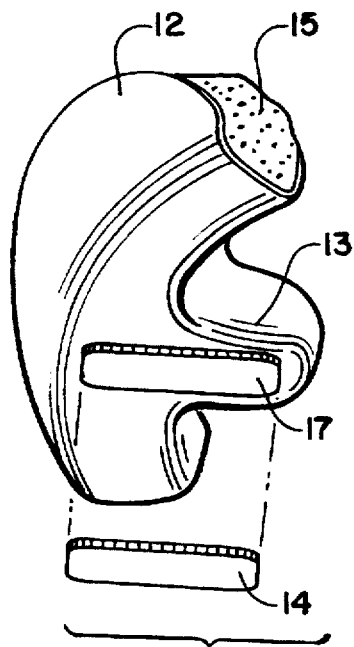
FIG. 4 is a perspective few of the semi-custom discluder device seen from the left-front-inferior, with the trough filled with acrylic resin and with one extending tab in place, and another extension tab aligned for placement.
Figure 5:
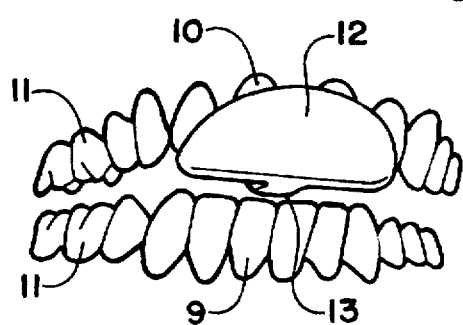
FIG. 5 is an anterior view of the semi-custom discluder device in function, secured onto the anterior maxillary incisors with the discluding dome opposing the mandibular incisors.

The semi-custom discluder 12 is shown in detail in FIGS. 2–4, which is a curved trough, similar to the curvature of the maxillary anterior teeth 10. Extending distally from the trough is a dome 13, which the lower anterior incisors 9 come into contact with as the mandible 16 elevates. The semi-custom discluder 12 is held in place on the anterior maxillary incisors 10 by a farmable acrylic material 15, that cures to a rigid state. The material is placed within the trough 12 by a dentist. The trough is then placed in the mouth, over the maxillary anterior incisors 10 and the resin is cured in place or after removal, as desired.

In the event that the posterior teeth 11 come into contact before the lower incisors 9 contact the dome 13 while the semi-custom discluder 12 is in place, extension tabs 14 can be adhered to the dome 13 by the wearer until such time that the lower incisors 9 contact the dome-with-tab complex 17 before the posterior teeth 11 contact.

Other applications, variations and ramifications of this invention will occur to those skilled in the art upon reading this disclosure. Those are intended to be included within the scope of this invention, as defined in the appended claims.

I claim:

1. An intraoral semi-custom discluding device which comprises:
   a prefabricated trough designed to encompass the anterior maxillary incisors;
   a dome on said trough extending distally when in a wearer's mouth;
   said dome configured to contact at least one lower anterior incisor when in place in said wearer's mouth prior to any contact between upper and lower posterior teeth; and
   a quantity of acrylic resin in said trough molded to conform to the shape of anterior maxillary incisors;
   whereby said trough is releasably retained in the mouth by said molded acrylic resin.

2. The device according to claim 1 wherein said trough and dome are fabricated from a synthetic resin.

3. The device according to claim 1 further including a plurality of tabs fastened over said dome to increase the height thereof as desired.

4. The method of preventing the occurrence of chronic tension and common migraine headaches and temporomandibular disorders which comprises the steps of:
   providing a device comprising a trough configured to encompass the upper anterior teeth, said trough having a dome that is retained by a resilient material;
   filling said trough with an uncured acrylic resin;
   fitting said device to a person's teeth with said dome extending toward said lower anterior incisors such that dome will contact at least one lower incisor tooth prior to any contact between posterior teeth;
   curing said acrylic resin;
   placing said device in said person's mouth for selected periods.

5. The method according to claim 4 wherein said trough and dome are fabricated from a synthetic resin sheet material.

6. The method according to claim 4 further including the steps of providing a plurality of synthetic resin sheet material tabs and of securing a selected number of tabs in a stacked relationship on said dome to adjust dome height as desired.

7. The method according to claim 4 further including the steps of providing a plurality of synthetic resin sheet material tabs and of securing a selected number of tabs in a stacked relationship on said dome to adjust dome height as desired.

8. A method of manufacturing a device for preventing the occurrence of chronic tension and common migraine headaches and temporomandibular disorders which comprises the steps of:
   providing a trough configured to encompass the upper anterior teeth, said trough having a dome projecting therefrom;
   filling said trough with an uncured acrylic resin;
   fitting said trough to a person's teeth with said dome extending toward said lower anterior incisors such that said dome will contact at least one lower incisor tooth prior to any contact between posterior teeth;
   curing said acrylic resin;
   removing said device from the person's mouth.

* * * * *